United States Patent
Can et al.

(10) Patent No.: US 8,135,187 B2
(45) Date of Patent: Mar. 13, 2012

(54) METHOD AND APPARATUS FOR REMOVING TISSUE AUTOFLUORESCENCE

(75) Inventors: Ali Can, Troy, NY (US); Michael John Gerdes, Albany, NY (US); Musodiq Olatayo Bello, Niskayuna, NY (US); Xiaodong Tao, Niskayuna, NY (US); Francis Edward Pavan-Woolfe, New Haven, CT (US); Roshni Bhagalia, Ann Arbor, MI (US)

(73) Assignee: General Electric Company, Niskayuna, NY (US)

( * ) Notice: Subject to any disclaimer, the term of this patent is extended or adjusted under 35 U.S.C. 154(b) by 1022 days.

(21) Appl. No.: 12/056,078

(22) Filed: Mar. 26, 2008

(65) Prior Publication Data
US 2009/0245611 A1    Oct. 1, 2009

(51) Int. Cl.
*G06K 9/00* (2006.01)
*A61B 1/06* (2006.01)

(52) U.S. Cl. ........ 382/128; 382/130; 600/109; 600/160; 435/6

(58) Field of Classification Search .......... 382/128–133; 600/160, 407–464
See application file for complete search history.

(56) References Cited

U.S. PATENT DOCUMENTS

| | | | | |
|---|---|---|---|---|
| 5,827,660 | A | * | 10/1998 | Singer et al. ............ 435/6 |
| 7,907,169 | B2 | * | 3/2011 | Sugimoto ............ 348/65 |
| 2002/0177149 | A1 | | 11/2002 | Rimm et al. |
| 2007/0016082 | A1 | * | 1/2007 | Levenson et al. ......... 600/476 |
| 2008/0031521 | A1 | | 2/2008 | Can et al. |
| 2008/0032321 | A1 | | 2/2008 | Ginty et al. |
| 2008/0032328 | A1 | | 2/2008 | Cline et al. |
| 2008/0033657 | A1 | | 2/2008 | Cline et al. |

FOREIGN PATENT DOCUMENTS

JP    08-334466    * 12/1996

OTHER PUBLICATIONS

Methodology article "LS-NMF: A modified non-negative matrix factorization algorithm utilizing uncertainty estimates" Guoli Wang et al Mar. 28, 2006.*

* cited by examiner

*Primary Examiner* — Melissa Koval
*Assistant Examiner* — Emily Chan
(74) *Attorney, Agent, or Firm* — Fletcher Yoder

(57) ABSTRACT

Techniques for removing image autoflourescence from fluorescently stained biological images are provided herein. The techniques utilize non-negative matrix factorization that may constrain mixing coefficients to be non-negative. The probability of convergence to local minima is reduced by using smoothness constraints. The non-negative matrix factorization algorithm provides the advantage of removing both dark current and autofluorescence.

21 Claims, 5 Drawing Sheets

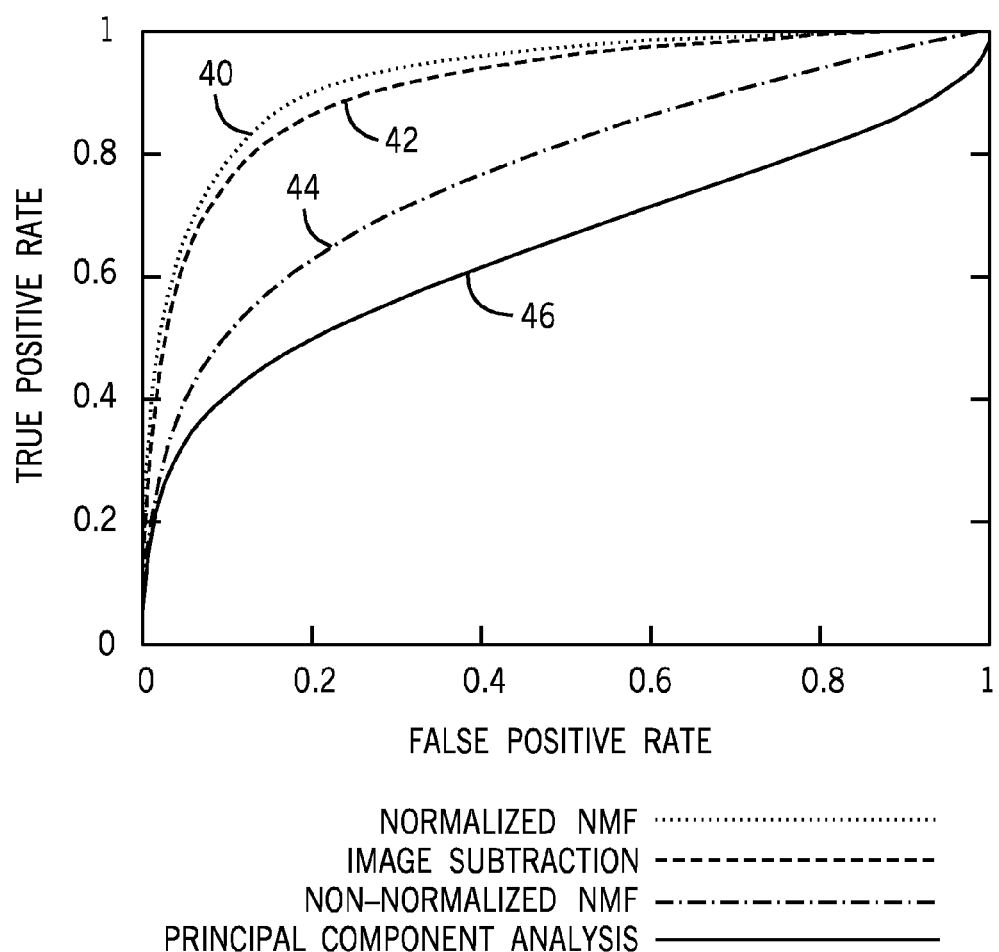

METHOD AND APPARATUS FOR REMOVING TISSUE AUTOFLUORESCENCE

BACKGROUND

The invention relates generally to methods and systems for removing inherent autofluorescence and the contribution of dark current from images of biological materials.

Recent advances in imaging and microscopy technologies combined with the development of fluorescent probes have allowed researchers to study variations in movement, distribution, and concentration of various molecular markers. In many such studies, fluorescent probes with a binding specificity to one or more cellular molecules are introduced into a sample. Images are obtained of the sample, for example with fluorescence microscopy, and these images may be processed and further analyzed to determine the amount of fluorescence in the image, which may provide information about the cellular marker. Accurate detection and analysis of the contribution of fluorescence from the fluorescent probes may be critical for many microscopy applications, such as molecular pathology imaging. For example, the fluorescence in the image may be analyzed to determine if the samples contain markers associated with specific clinical conditions, such as cancer.

Cells in many organisms have inherent fluorescence, which may be referred to as autofluorescence. This autofluorescence can interfere with the analysis of images obtained of these cells. For example, autofluorescence may reduce signal detection sensitivity by masking the fluorescence of the probe of interest. In addition, autofluorescence may also decrease the specificity of detection by providing false positive results.

The extent of autofluorescence may be limited by treating the sample with certain dyes or chemicals prior to image acquisition. For example, the dye pontiamine sky blue is used to stain samples and quench autofluorescence. However, these treatment techniques involve further manipulation of the biological sample, which may degrade the quality of the sample itself. In addition, strategies for autofluorescence removal have been proposed that involve the image acquisition hardware, such as using lasers for excitation or polarized light. However, these techniques may not be suitable with standard fluorescent microscopes in widespread use.

Digitally acquired fluorescence microscope images can also be processed retrospectively using software methods, to separate autofluorescence from the relevant dye fluorescence. Some of these methods rely on acquiring estimates of the pure autofluorescence signal and using them to remove autofluorescence from images containing both dye and autofluorescence signals by a weighted subtraction. Others use statistical correlation techniques to correct for the additive autofluorescence signal. While these techniques may be more cost effective, they may not be able to completely remove the autofluorescence component from fluorescence microscopy images. For example, spectral unmixing methods often require prior knowledge of the amount of autofluorescence in the sample.

In addition, cell or tissue images may also include a certain amount of noise contributed by the acquisition system itself. For example, "dark current," represents the response, in the absence of light, of many types of electromagnetic radiation receptors. Generally, dark current is dealt with by a simple subtraction. However, there is no image processing method that deals with both autofluorescence and dark current.

BRIEF DESCRIPTION

The methods and systems of the invention generally involve a fully automated technique for the removal of autofluorescence from various images, each containing an unknown combination of autofluorescence and fluorescence of interest. The acquired images may be subjected to a non-negative matrix factorization algorithm to remove autofluorescence. In addition, the methods and systems of the invention also remove dark current noise from the fluorescent images.

The present techniques provide a method for reducing autofluorescence in an image of a biological material that includes: accessing image data from two or more images of the biological material, wherein at least one of the images is fluorescently stained for a marker of interest and wherein at least one of the images is a reference image; analyzing the image data of the two or more images using a non-negative matrix factorization algorithm to generate an estimate of the autofluorescence in at least one of the two or more images; and generating an output of a corrected image with reduced autofluorescence.

The present techniques also provide a computer-readable medium that includes instructions for: accessing image data from two or more images of the biological material, wherein at least one of the images is fluorescently stained for a marker of interest and wherein at least one of the images is a reference image; analyzing the image data of the two or more images using a non-negative matrix factorization algorithm to generate an estimate of the autofluorescence in at least one of the two or more images; and generating an output of a corrected image with reduced autofluorescence.

The present techniques also provide an image analysis system that includes a processor adapted to receive image data from two or more images of the biological material, wherein at least one of the images is fluorescently stained for a marker of interest and wherein at least one of the images is a reference image the processor adapted to run instructions for: analyzing the image data of the two or more images using a non-negative matrix factorization algorithm to generate an estimate of the autofluorescence in at least one of the two or more images; and generating an output of a corrected image with reduced autofluorescence.

DRAWINGS

These and other features, aspects, and advantages of the present invention will become better understood when the following detailed description is read with reference to the accompanying drawings in which like characters represent like parts throughout the drawings, wherein:

FIG. 4 shows mean receiver operator characteristic curves (ROCs) for 35 tissue samples;

DETAILED DESCRIPTION

The methods and systems of the present techniques may provide the advantage of improving image analysis for fluorescently stained images. Such techniques may preserve signal fluorescence while reducing or eliminating autofluorescence, as well as dark current. The techniques increase the resulting signal-to-autofluorescence ratio and the overall sensitivity of detection. These fully automatic systems and methods operate without user intervention and complicated and expensive instrumentation. The methods and systems are adaptable to a wide array of biological samples, including tissue micro arrays. However, they are not limited to use with tissue micro arrays and may be applied to any fluorescence imaging application.

The present techniques provide an automatic autofluorescence removal method for fluorescent spectroscopy, based on a realistic physical model. In one embodiment, the image processing technique provided herein uses a non-negative matrix factorization algorithm with reduced probability for convergence to local minima. Smoothing the estimated autofluorescence and autofluorescence-reduced images at every stage of the iteration with a Gaussian kernel helps to constrain the computed solution by taking into account that changes in the image on a scale smaller than the standard deviation of the kernel may be irrelevant to the analysis. Unlike previous spectral mixing models used for autofluorescence removal, the method provided herein may utilize a mixing matrix that is estimated from image data, rather than being provided by the user. In addition, because the matrices used in the method have non-negative entries, a model may be generated that is physically interpretable. Furthermore, the algorithm provided herein automatically compensates for unknown dark current terms, $d_i$, that may be present in images acquired by fluorescent microscopy. This is achieved by the novel non-negative matrix factorization algorithm used by the present techniques.

Figure 1:
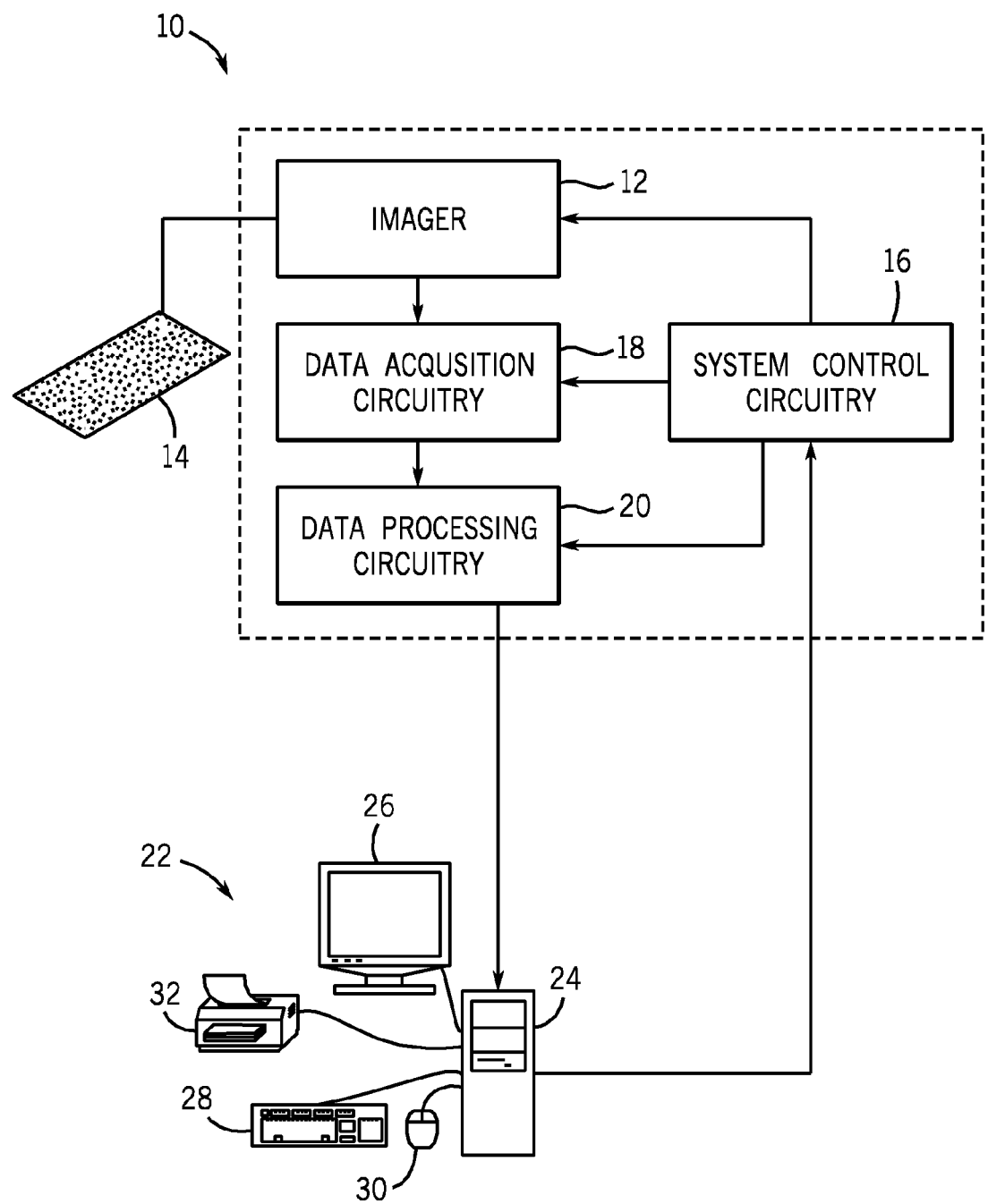
FIG. 1 is a diagrammatical view of an exemplary system for use in acquiring image data of cells in accordance with aspects of the present technique.

The present techniques provide systems and methods for image analysis. In certain embodiments, it is envisioned that the present techniques may be used in conjunction with previously acquired images, for example, stored images, in retrospective studies. In other embodiments, the present techniques may be used in conjunction with an image acquisition system. An exemplary imaging system 10 capable of operating in accordance with the present technique is depicted in FIG. 1. Generally, the imaging system 10 includes an imager 12 that detects signals and converts the signals to data that may be processed by downstream processors. As described more fully below, the imager 12 may operate in accordance with various physical principles for creating the image data. In certain embodiments, the imager 12 may include a fluorescent microscope or other suitable imager for analyzing fluorescently stained images. In general, however, the imager 12 creates image data indicative of a biological sample, including a sample 14, shown here as being multiple samples on a tissue micro array. The image data may be either in a conventional medium, such as photographic film, or in a digital medium.

The imager 12 operates under the control of system control circuitry 16. The system control circuitry 16 may include a wide range of circuits, such as illumination source control circuits, timing circuits, circuits for coordinating data acquisition in conjunction with sample movements, circuits for controlling the position of light sources and detectors, and so forth. In the present context, the system control circuitry 16 may also include computer-readable memory elements, such as magnetic or optical storage media, for storing programs and routines executed by the system control circuitry 16 or by associated components of the system 10. The stored programs or routines may include programs or routines for performing all or part of the present technique.

Image data acquired by the imager 12 may be processed by the imager 12, for a variety of purposes, for example to convert the acquired data or signal to digital values, and provided to data acquisition circuitry 18. The data acquisition circuitry 18 may perform a wide range of processing functions, such as adjustment of digital dynamic ranges, smoothing or sharpening of data, as well as compiling of data streams and files, where desired.

The data acquisition circuitry 18 may also transfer acquisition image data to data processing circuitry 20, where additional processing and analysis may be performed. Thus, the data processing circuitry 20 may perform substantial analyses of image data, including ordering, sharpening, smoothing, feature recognition, and so forth. In addition, the data processing circuitry 20 may receive data for one or more sample sources, (e.g. multiple spots on a tissue micro array). The processed image data may be stored in short or long term storage devices, such as picture archiving communication systems, which may be located within or remote from the imaging system 10 and/or reconstructed and displayed for an operator, such as at the operator workstation 22.

In addition to displaying the reconstructed image, the operator workstation 22 may control the above-described operations and functions of the imaging system 10, typically via an interface with the system control circuitry 16. The operator workstation 22 may include one or more processor-based components, such as general purpose or application specific computers 24. In addition to the processor-based components, the computer 24 may include various memory and/or storage components including magnetic and optical mass storage devices and internal memory, such as RAM chips. The memory and/or storage components may be used for storing programs and routines for performing the techniques described herein that are executed by the computer 24 or by associated components of the system 10. Alternatively, the programs and routines may be stored on a computer accessible storage and/or memory remote from the operator workstation 22 but accessible by network and/or communication interfaces present on the computer 24.

The computer 24 may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

More than a single operator workstation 22 may be provided for an imaging system 10. For example, an imaging scanner or station may include an operator workstation 22 which permits regulation of the parameters involved in the image data acquisition procedure, whereas a different operator workstation 22 may be provided for manipulating, enhancing, and viewing results and reconstructed images.

These methods and systems may be used to image and analyze a biological sample to discern the presence, absence, concentration, and/or spatial distribution of one or more biological materials or targets in a biological sample or tissue. As used herein, the term "biological material" refers to material obtained from, or located in, a biological subject, including samples of biological tissue or fluid origin obtained in vivo or in vitro and biological materials that may be located in situ. Such samples can be, but are not limited to, body fluid (e.g., blood, blood plasma, serum, or urine), organs, tissues, fractions, and cells isolated from, or located in, mammals including, humans. Biological samples also may include sections of the biological sample including tissues (e.g., sectional portions of an organ or tissue). Biological samples may also include extracts from a biological sample, for example, an antigen from a biological fluid (e.g., blood or urine). Further, the biological sample may include two or more samples that form a tissue micro array.

A biological material may include any material regardless of its physical condition, such as, but not limited to, being frozen or stained or otherwise treated. In some embodiments, a biological material may include a tissue sample, a whole cell, a cell constituent, a cytospin, or a cell smear. In other embodiments, a biological material may be an in situ tissue target, if successive images of the targeted tissue can be obtained, first with the reference dye and subsequently with the additional dyes. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In some embodiments, a biological sample includes tissue sections from healthy or diseased tissue samples (e.g., tissue sections from colon, breast tissue, prostate). A tissue section may include a single part or piece of a tissue sample, for example, a thin slice of tissue or cells cut from a tissue sample. In some embodiments, the same section of tissue sample may be analyzed at both morphological and molecular levels.

As used herein, the term "fluorescent imaging agent" refers to fluorophores that are chemical compounds, which when excited by exposure to a particular wavelength of light, emit light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, pyrelium dyes, and squaraines.

For applications that additionally use probes, as used herein, the term "probe" refers to an agent having a binder and a label, such as a signal generator. In some embodiments, the binder and the label are embodied in a single entity. The binder and the label may be attached directly (e.g., via a fluorescent molecule incorporated into the binder) or indirectly (e.g., through a linker, which may include a cleavage site) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label are separate entities they may be applied to a biological sample in a single step or multiple steps. As used herein, the term "fluorescent probe" refers to an agent having a binder coupled to a fluorescent signal generator. These methods and systems are not limited to any specific imaging agents, morphological dyes, biomarkers or probes. Any fluorescent or non-fluorescent dye or imaging agent that enables some informative aspect or feature of a biological material to be actually or artificially visualized so that it can be digitally imaged and processed, would be suitable. Suitable dyes and imaging agents include, but are not necessarily limited to, cytological or morphological dyes, immunological dyes such as immunohisto- and immunocytochemistry dyes, cytogenetical dyes, in situ hybridization dyes, cytochemical dyes, DNA and chromosome markers, and substrate binding assay dyes.

The methods and systems may be adapted for, but are not limited to, use in analytical, diagnostic, or prognostic applications such as analyte detection, histochemistry, immunohistochemistry, or immunofluorescence. In some embodiments, the methods and systems may be particularly applicable in histochemistry, immunostaining, immunohistochemistry, immunoassays, or immunofluorescence applications. In some embodiments, the methods and systems may be particularly applicable in immunoblotting techniques, for example, western blots or immunoassays such as enzyme-linked immunosorbent assays (ELISA).

Figure 2A:
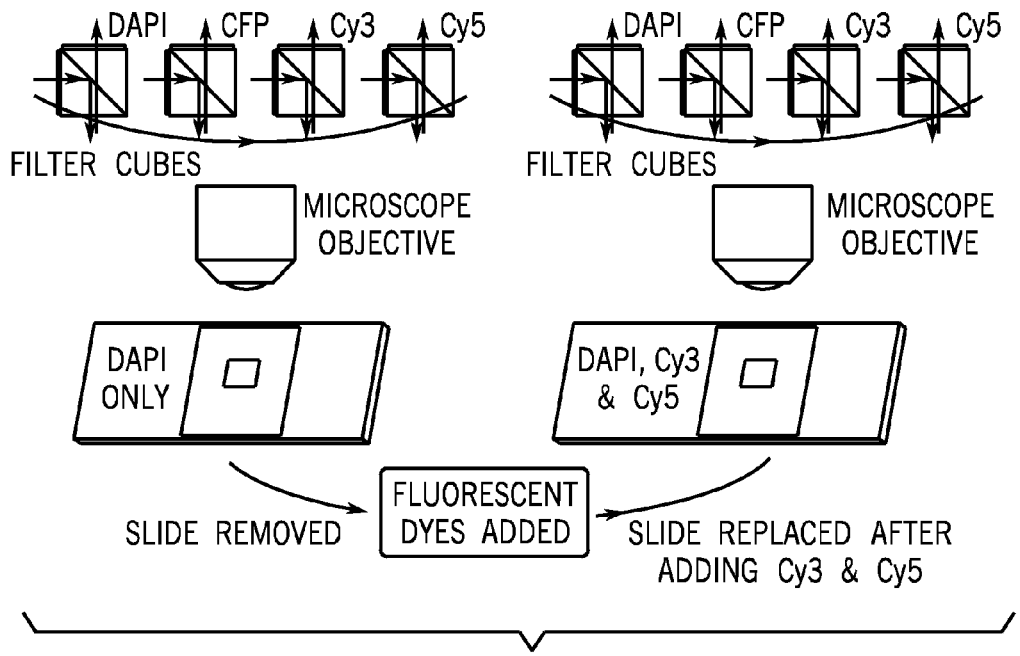
FIG. 2A is a diagrammatical view of an exemplary two-step image acquisition system in accordance with aspects of the present technique.
Figure 2B:
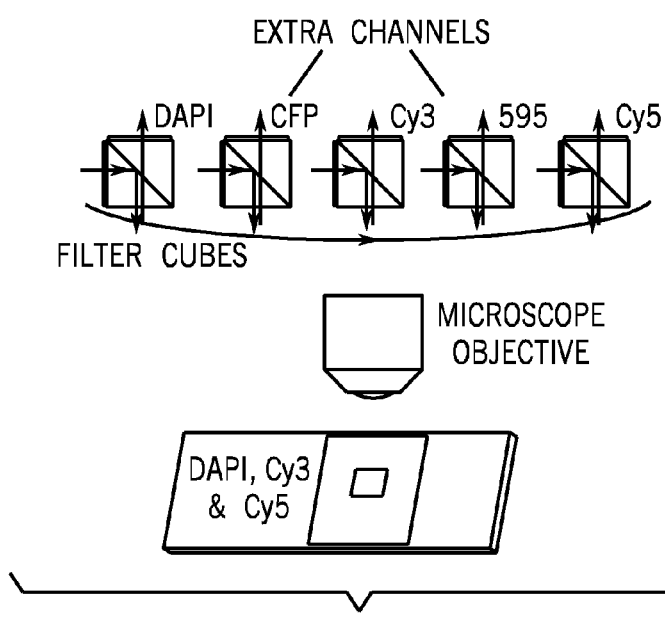
FIG. 2B is a diagrammatical view of an exemplary extra channel image acquisition system in accordance with aspects of the present technique.

FIGS. 2A and 2B illustrate techniques that may be employed to acquire images for use in certain embodiments. FIG. 2A is a schematic diagram of a two-step method of image acquisition suitable for use with the present techniques. In the first step, only one fluorescent dye, e.g., DAPI is used to stain the tissue. A pre-determined set of four filter cubes may be used sequentially to obtain images of the DAPI emission wavelength as well as wavelengths associated with CFP, Cy3 and Cy5 tissue autofluorescence emission wavelengths. In the second step, the tissue sample is removed from the microscope and immunostained with additional fluorescent dyes that are associated with probes or other molecules specific for a marker of interest. The procedure mentioned above is then repeated on this stained tissue sample to acquire another set of images using the same four wavelengths. These images contain an unknown combination of autofluorescence, Cy3 and Cy5 dye signals from the four channels. In one embodiment, the images acquired from the first step are registered with images obtained from the second step, using the DAPI channel as a registration guide. Following registration using the DAPI channel, the present techniques may be used to estimate the autofluorescence of the images. An advantage of the two-step method is that the autofluorescence estimate is obtained at the same part of the spectrum as the fluorescence due to dye. In addition to providing information about nuclear location in the images, DAPI acquired in both steps are used to register the two image sets. However the DAPI images contain only local image features. An additional autofluorescence image at wavelengths between the DAPI and Cy3 response channels is obtained, using a filter cube matched to the spectral response of Cyan Fluorescent Protein (CFP). Note that since the tissue sample is not stained with CFP, this image captures only the autofluorescence signal and is characterized by global image features. Thus, to combine both global and local feature information for image registration purposes, the DAPI and CFP images can be added to form composite images.

In general, given a pair of observed tissue images $X1_{obvs}$ and $X2_{obvs}$ with different dye signal to autofluorescence ratios, the images are related to the underlying true (autofluorescence-free) dye and the separated autofluorescence images as follows;

$$\left. \begin{array}{l} X1_{obvs} = a_{11}X_{dye} + a_{12}X_{af} \\ X2_{obvs} = a_{21}X_{dye} + a_{22}X_{af} \end{array} \right\} \Rightarrow \begin{bmatrix} X1_{obvs} \\ X2_{obvs} \end{bmatrix} = \begin{bmatrix} a_{11} & a_{12} \\ a_{21} & a_{22} \end{bmatrix} \begin{bmatrix} X_{dye} \\ X_{af} \end{bmatrix} \quad (1)$$

In the two-step experiment, there are two image observations for each dye channel, with one image being purely autofluorescence in that channel. Thus, denoting the pair of images from each channel by $X1_{obvs}$ and $X2_{obvs}$ the above equation becomes;

$$\begin{bmatrix} X1_{obvs} \\ X2_{obvs} \end{bmatrix} = \begin{bmatrix} 0 & a_{12} \\ a_{21} & a_{22} \end{bmatrix} \begin{bmatrix} X_{dye} \\ X_{af} \end{bmatrix} \quad (2)$$

In cases where the number of tissue samples to be analyzed is large, it may not be practical to use the two-step procedure for image acquisition. Furthermore, a single step process may provide the advantage of reduced artifacts being introduced in the images due to image registration as well as damage to the tissue during removal of the coverslip before immunostaining. Accordingly, in certain embodiments it may be advantageous to acquire images using an "extra-channel" method, a schematic diagram of which is shown in FIG. 2B. The extra-channel method is a single step method that acquires images of the stained tissue, with varying dye signal to autofluorescence ratios, in more channels than there are dyes.

In the extra-channel method, the tissue sample is stained with DAPI and immunostained with antibodies conjugated to Cy3 and Cy5. Other than the three filter cubes matched to the emission spectra of the three dyes, the extra-channel method may use three extra cubes matched to CFP and far-red light at both 595 nm (RED1) and 624 nm (RED2). In one embodiment, the CFP channel measures the autofluorescence signal similarly to that from the Cy3 channel, and, for example, the filters at 595 nm and 695 nm record an unknown mixture of the excitations from tissue autofluorescence and dyes in the Cy3 and Cy5 channels.

The autofluorescence spectrum is generally wide-band and dye-independent. Hence, images of the autofluorescence signal at wavelengths close to, but not coinciding with, those of the Cy3 and Cy5 dye emission spectra can be used to estimate and subsequently remove the spectrum of the autofluorescence signal in the dye channels according to the present techniques.

The present techniques may be used to model the additional observations from the extra-channel method. These observations are a combination of varying ratios of Cy3 signal to the autofluorescence at the Cy3 emission wavelength and Cy5 dye signal to Cy5 channel autofluorescence. The observed images may be modeled as unknown linear combinations of the tissue autofluorescence and autofluorescence-free dye images in the five observation channels, namely Cy3, Cy5, CFP, RED1 and RED2. The images from Cy3 and CFP are primarily Cy3 dye and Cy3 autofluorescence signals, respectively $$CY3_{obvs} = a_{11} \times CY3_{dye} + a_{12} \times CY3_{af}$$

$$CFP_{obvs} = a_{22} \times CY3_{af} \quad (3a)$$

Similarly the observed images from the Cy5 and RED channels are related to the true dye and autofluorescence signals as;

$$RED1_{obvs} = a_{31} \times CY3_{dye} + a_{32} \times CY3_{af} + a_{33} \times CY5_{dye} + a_{34} \times CY5_{af}$$

$$RED2_{obvs} = a_{42} \times CY5_{dye} + a_{43} \times CY3_{af} + a_{44} \times CY5_{af}$$

$$CY5_{obvs} = a_{53} \times CY5_{dye} + a_{54} \times CY5_{af} \quad (3b)$$

Equations (3a) and (3b) are valid for all pixels that do not belong to the background of any observed image appearing in that equation. In matrix form, equations (3a) and (3b) can be written as:

$$\begin{bmatrix} CY3_{obvs} \\ CFP_{obvs} \\ RED1_{obvs} \\ RED2_{obvs} \\ CY5_{obvs} \end{bmatrix} = \begin{bmatrix} a_{11} & a_{12} & 0 & 0 \\ 0 & a_{22} & 0 & 0 \\ a_{31} & a_{32} & a_{33} & a_{34} \\ 0 & a_{42} & a_{43} & a_{44} \\ 0 & 0 & a_{53} & a_{54} \end{bmatrix} \begin{bmatrix} CY3_{dye} \\ CY3_{af} \\ CY5_{dye} \\ CY5_{af} \end{bmatrix} \quad (4)$$

The present techniques also account for sizeable interactions between the Cy3 and Cy5 channels. For instance, the model allows possibly significant cross talk between Cy3 and Cy5 images, even though the theoretical responses of these channels indicate that there is minimal overlap between the spectra of the two channels. This is done in anticipation of the observed red-shift of emission spectra in tissue samples. Since no prior knowledge of the proportions in which the different true images contribute to the observations is assumed, both the matrix of mixing coefficients and the vector of true image pixels on the right hand side of equation (4) are unknown. Physical observations indicate that the true dye and autofluorescence images may be assumed to be statistically independent making the system of equations solvable.

Expression of a specific protein or structure in the autofluorescence image of a tissue sample is no indication of its presence or absence in an image of the sample after a protein-specific dye has been used to stain it. Random observations may be statistically independent if the presence of one gives no information about the other. Mathematically, random vectors x and y may be statistically independent if and only if their joint probability density can be factorized into a product of their marginal probability densities;

$$P(x,y)=P_X(x) \times P_Y(y) \tag{5}$$

It follows that the true autofluorescence image of a tissue spot is statistically independent of its true (autofluorescence-free) dye image. This is true for many applications. Exceptions are situations in which the biomarker binds to a tissue structure (e.g. lipid droplet) that has significant intrinsic autofluorescence, distinct from other tissue components.

Since the dyes are targeted to detect specific proteins and the AF signals have tissue-dependent pixel intensities, these images can be assumed to be observations drawn from non-Gaussian, often bimodal, distributions.

Regardless of the manner in which the images are acquired, the present techniques may be applied to the acquired images in order to reduce and/or remove any inherent autofluorescence in the images. In one embodiment, the present techniques provide a Joint Estimation Technique that includes Non-negative Matrix Factorization. Non-negative Matrix Factorization (NMF) is a technique of decomposing a matrix of non-negative observations into a product of two matrices, each of which has only non-negative elements. NMF may use the Euclidean squared distance cost function and the corresponding multiplicative update rule.

The present techniques allow observed images to be described as unknown linear combinations of an underlying signal image (due to fluorescence of interest) and an autofluorescence image, plus an unknown offset, due to dark current. The term m may be defined to be the number of such images acquired and the term n to be the number of pixels in each image while the term $e_i$ may be defined to be the camera exposure time for the $i^{th}$ image, where i is any integer such that $0 \leq i \leq m$. The values $e_i$ may be recorded when the images are acquired and, thus, may be a known parameter input to the present techniques. In specific embodiments, charge-coupled device cameras attached to fluorescent microscopes, like many other radiation receptors, exhibit a constant response even in the absence of light. This offset, known as "dark current" may vary, for example due to changes in temperature. The non-negative real number $d_i$ may be defined to be the dark current for the $i^{th}$ image, where i is an integer such that $0 \leq i \leq m$. The variable $d_i$ is constrained to be non-negative since dark current effects are always additive. The values $d_i$ are unknown parameters of the present model. The real 1×n row vector is defined as $I_{OBS}^i$, whose entries are the pixels of the $i^{th}$ acquired image, where i, is an integer such that $0 \leq i \leq m$. The $i^{th}$ entry of the real 1×n row vector $I_{AF}$, is defined to be the intensity of autofluorescence due to tissue at pixel location j, for each integer j such that $1 \leq j \leq n$. The $j^{th}$ entry of the real 1×n row vector $I_{SIG}$ is defined to be the intensity of fluorescence of interest at pixel location j, for each integer j such that $1 \leq j \leq n$. In one embodiment, $I_{OBS}^i$ is a linear combination of $I_{AF}$ and $I_{SIG}$ with coefficients given by the equation $$I_{OBS}^i = e_i((b_{i,1} \times I_{SIG}) + (b_{i,2} \times I_{AF}) + d_i), \tag{6}$$

where $b_{i,1}$ and $b_{i,2}$ are non-negative real numbers, for every integer i such that $1 \leq i \leq m$. Equation (6) is a spectral mixing model, and represents the physical situation giving rise to the observed images. More specifically, the observed images $I_{OBS}^i$ are written as linear combinations of two underlying images: $I_{SIG}$ (denoting the fluorescence of interest), and $I_{AF}$ (denoting the autofluorescence). The unknown dark current terms $d_i$ and the known exposure times $e_i$ act as a shift and a scale factor (respectively).

The algorithm of the present techniques may estimate $b_{i,1}$, $b_{i,2}$, $I_{AF}$, and $I_{SIG}$ given $I_{OBS}^i$ for each integer i such that $0 \leq i \leq m$. In other words, the algorithm calculates an image (denoted $I_{AF}$) that represents autofluorescence and an image (denoted $I_{SIG}$) which represents fluorescence of interest. In addition, the algorithm calculates coefficients $b_{i,j}$ which specify how the images $I_{AF}$ and $I_{SIG}$ are combined to form the observed images (denoted $I_{OBS}^i$), each of which may contain some autofluorescence and some fluorescence of interest.

In certain embodiments of the present technique, a matrix A may be defined as the real m×n matrix A according to the formula $$A = \begin{bmatrix} I_{OBS}^1 \\ \vdots \\ I_{OBS}^m \end{bmatrix}, \tag{7}$$

where $I_{OBS}^i$ is defined in equations (3a) and (3b), for each integer i such that $1 \leq i \leq m$. The images in the rows of A are the inputs to the algorithm and contain unknown mixtures of autofluorescence and fluorescence of interest plus an unknown dark current term times a known exposure time. The matrix A is defined as the observation matrix. The entries of A are non-negative since they represent image pixels.

In certain embodiments of the present technique, a matrix C may be defined as the real 2×n matrix C according to the formula $$C = \begin{bmatrix} I_{SIG} \\ I_{AF} \end{bmatrix}, \tag{8}$$

The first row of C contains an estimate of the component due to fluorescence of interest, in the images in the matrix A. The second row of C contains an estimate of the component due to autofluorescence, in the images in the matrix A. The matrix C is known as the source matrix. The entries in C are non-negative since they represent image pixels.

In certain embodiments of the present technique, a matrix B may be defined wherein the (i,j) entry of the real i×2 matrix B may be $b_{i,j}$, where $b_{i,j}$ satisfies equation (6), for any integers i and j such that $1 \leq i \leq m$ and $1 \leq j \leq n$. The entries in B specify how much autofluorescence and how much fluorescence of interest is present in each of the images in A, according to equation (6). More specifically, $b_{i,1}$ and $b_{i,2}$ specify how much fluorescence of interest and autofluorescence (respectively) is in $I_{OBS}^i$, for any integer i such that $1 \leq i \leq m$, where $I_{OBS}^i$ is defined in equations (3a) and 3(b). It follows that the ratio of autofluorescence to fluorescence of interest in the image in the $i^{th}$ row of A is $$\frac{b_{i,2}}{b_{i,1}}, \qquad (9)$$

for any integer i such that $1 \leq i \leq m$. The matrix B is known as the mixing matrix. Since the entries of B are non-negative, equation (6) is physically interpretable.

In certain embodiments of the present technique, a matrix D may be defined wherein the (i,j) entry of the real m×n matrix D may be $d_i$, defined in equation (6). It follows that all columns of D are identical, and hold the dark currents $d_j$, of each of the m images. Since dark current acts additively, the variables $d_j$, are constrained to be non-negative, so the entries of D are all non-negative.

In certain embodiments of the present technique, a matrix E may be defined to be the real, diagonal, m×m matrix with the exposure times of the observed images $I_{OBS}^i$ as diagonal entries. In other words, the $i^{th}$ diagonal entry of E is defined to be where the term $e_i$, is defined in equation (1), and i is any integer such that $0 \leq i \leq M$. Since $e_i$ represents time, all the entries in E are non-negative.

It follows from equation (6), and the definitions of A, B, C, D, and E, respectively, that $$A = E(BC+D). \qquad (11)$$

All the entries in all the matrices in equation (11) are non-negative. Therefore, the model of the present techniques constitutes a non-negative matrix factorization model for autofluorescence of biological tissue, acquired by an imaging device with a variable dark current term, such as a charge-coupled device camera attached to a fluorescent microscope. Because the exposure times in the matrix E and the dark current terms in the matrix D are part of the model, equation (11) is a normalized non-negative matrix factorization.

One disadvantage of previous non-negative matrix factorization algorithms has been convergence to local minima. The present algorithm includes a novel step designed to reduce these occurrences using a Gaussian kernel to smooth the images at every iteration. In certain embodiments, the smoothing factor is reduced at later iterations, and the final iterations may continue without any smoothing. Regularization of the computed solution incorporates the prior knowledge that changes in the image on a scale smaller than the standard deviation of the kernel are irrelevant. This helps to constrain the solution computed by the algorithm, reducing the probability of undesirable local minima.

An alternating constrained least squares approach may be used to solve equation (11). The matrices B and C may be initialized in an application-specific way. Then, the following three steps may be repeated until convergence. The first step is to estimate B and D, holding C fixed. The second step is to estimate C, holding B, and D fixed. The third step is to smooth the images in the rows of C, using a Gaussian kernel, whose standard deviation decreases with each iteration. The initialization of B, C, and D depends on the specific circumstances under which the algorithm is used.

The first step of the present algorithm is to estimate B and D, holding C fixed. More specifically, the new matrices B and D solve the optimization problem $$[B|D] = \underset{\{\tilde{B},\tilde{D}: \tilde{b}_{i,j} \geq 0, \tilde{d}_{i,j}\}}{\operatorname{argmin}} \left\| A - E[B|D]\begin{bmatrix} C \\ 1 \end{bmatrix} \right\|. \qquad (12)$$

That is, the matrices B and D minimize the reconstruction error $\|A-E[B|D][C/1]\|$ subject to the constraint that all entries in B and D must be non-negative. Equation (12) is an instance of a non-negatively constrained least squares problem. A solution to a non-negatively constrained least squares problem is a vector that satisfies a set of linear equations with minimal error, subject to having only non-negative entries. Suppose p, and q are positive integers. Suppose M is a real p×q matrix, and y is a real p×1 column vector. The non-negatively constrained least squares problem is to find a real q×1 column vector, x, such that $$\|mx-y\| \qquad (12.1)$$

is as small as possible, subject to the constraint that for each integer i, such that $1 \leq i \leq q$, (12.2) and $x_i \geq 0$. The algorithm minimizes (12.1) subject to (12.2). Suppose that w, and z are real q×1 column vectors. Suppose that Mp is a real p×q matrix. Suppose that P, and Z are sets of integers. The set P contains the indices of the non-zero (active) variables in the current solution x, and Z contains the indices of the zero (inactive) variables, in the current solution, x. The vector w is the dual vector of x.

The second step of the present algorithm is to estimate C, holding B and D fixed. More specifically, the new matrix C solves the optimization problem $$C = \underset{\{\tilde{C}: \tilde{c}_{i,j} \geq 0\}}{\operatorname{argmin}} \|A - E(BC+D).\| \qquad (13)$$

That is, the matrix C minimizes the reconstruction error $\|A-E(BC+D)\|$ subject to the constraint that all entries in C must be non-negative. Equation (13) is an instance of a non-negatively constrained least squares problem that may be solved as described herein.

The third step of the present algorithm is to smooth the images $I_{SIG}$ and $I_{AF}$, in the rows of C. Every pixel value is replaced by a weighted average of nearby pixel values. The weights are given by a Gaussian kernel $$\frac{1}{\sqrt{2\pi\sigma^2}} e^{\frac{r^2}{2\sigma^2}}. \qquad (14)$$

where r is the distance to the current pixel. The value of the parameter a decreases at each iteration. This step of the algorithm is designed to regularize the convergence of the algorithm, thus reducing the risk of converging into local minima.

In specific embodiments of the present techniques, as defined in equation (7) A has m rows of length n, each of which contains an image acquired according to the present techniques. For the purposes of the examples provided below, the number of images used in each run of the algorithm was m=4 and the number of pixels in each image was n=1205824. The term $J_{OBS}^{i,j}$ may be defined to be the image acquired in step i of the examples provided herein, using filter cube number j, where i and j are positive integers. The specific images in the rows of A either $$A = \begin{bmatrix} J_{OBS}^{4,5} \\ J_{OBS}^{2,5} \\ J_{OBS}^{2,1} \\ J_{OBS}^{4,1} \end{bmatrix} \quad (17)$$

$$A = \begin{bmatrix} J_{OBS}^{4,5} \\ J_{OBS}^{2,5} \\ J_{OBS}^{2,4} \\ J_{OBS}^{4,4} \end{bmatrix} \quad (18)$$

where $J_{OBS}$ is defined above. Row 1 of A contains an extra channel autofluorescence estimate. Rows 2 and 3 of A contain two step autofluorescence estimates. Row 4 contains an image intended to capture as much signal as possible with as little autofluorescence as possible. When A is defined by equation (17) (respectively, equation (18)), the image in row 4 is intended to capture as much fluorescence due to cy5 (respectively, cy3) as possible, with as little autofluorescence as possible.

As defined in equations (2) and (3), the matrix D has n identical columns of length m, each of which contains dark current estimates $d_i$ for the observed images $I_{OBS}^i$. The dark current estimate $d_i$ for $I_{OBS}^i$ is initialized to the 5$^{th}$ percentile of the image histogram of $I_{OBS}^i$. That is, $d_i$ is the value of a pixel in $I_{OBS}^i$ which is brighter than exactly 5 percent of pixels in $I_{OBS}^i$. These values are updated at each iteration of the non-negative matrix factorization algorithm.

As defined in equations (4), (5), and (8), the first row of C is $I_{SIG}$ (an estimate for the fluorescence of interest), and the second row of C is $I_{AF}$ (an estimate for the autofluorescence). The second row of C is initialized to a weighted average of the rows of A containing either two step or extra channel autofluorescence estimates, which are normalized by subtraction of the estimated dark current and division by the exposure time. To be more precise, for each integer i such that $1 \leq i \leq m-1$, $$\text{(row 2 of } C) = \Sigma_{i=1}^{m-1} w_i ((\text{row i of } A) - d_i)/e_i, \quad (19)$$

where the rows of A are as defined in equation (17) or (18), $d_i$ has the values described in the previous paragraph, and $e_i$ is defined in equation (1). The values of the weights $w_i$ in equation (19) are $$w_1 = \frac{1}{4}, w_2 = \frac{1}{4}, w_3 = \frac{1}{2}. \quad (20)$$

The matrix B is initialized by solving the optimization problem $$b = \operatorname*{argmin}_{\{\tilde{B} : \tilde{b}_{i,j} \geq 0\}} \left\| A - E\left([B|D]\begin{bmatrix} C \\ 1 \end{bmatrix}\right) \right\| \quad (21)$$

where the matrices A, C, and D initialized as described in the previous two paragraphs, and the matrix E is defined above. Equation (21) is an instance of a non-negatively constrained least squares problem. The value of the parameter σ, introduced in equation (14) was defined to be 2 in the first iteration, 1.8 in the second iteration, 1.6 in the third iteration 1.4 in the fourth iteration, 1.2 in the third iteration, 1 in the fifth iteration, and 0 in all subsequent iterations.

With the forgoing in mind, the following examples provide specific embodiments in which the present techniques have been applied. The concentration of antigens such as estrogen receptor, PCAD, and HER2 in human breast biopsies was analyzed. Fluorescent dyes in the cyanine family (cy3 and cy5) were bound to these antigens by using a corresponding antibody. In addition, the dye 4',6-diamidino-2-phenylindole DAPI) was used to stain cell nuclei. A fluorescence microscope and filters as described herein were used to excite the dyes and measure corresponding emission. The autofluorescence separation algorithm described above was used to separate the fluorescence due to dye with that due to tissue.

The experimental protocol used multiplexing, which refers to staining a sample with more than one dye at a time, removing that dye, staining again, and repeating the process many times over. The samples were initially stained with DAPI and then images were taken with each of the filter cubes listed in Table I. The samples were then stained with Cy3 bound to PCAD, and Cy5 bound to estrogen receptor. Images were then taken with each of the filter cubes listed in Table I. When the samples were removed from the stage and then replaced, the location on the stage is inevitably slightly different, so the images taken were then registered to compensate for the misalignment. This was accomplished using a technique based on mutual information.

In one application of the present techniques, fluorescent beads having a diameter of 1 micron (Polysciences Inc., Warrington, Pa., catalog number 18660) were embedded in tissue samples. A fluorescence microscope (axio imager upright model from Carl Zeiss, with a SCAN 130×85 piezodrive stage manufactured by Marzhauser Wetziar) was used to excite the samples and measure the corresponding emission. Images were acquired of the sample both before and after addition of fluorescent beads. Filters, called "excitation filters", were used to block light not having wavelengths in a certain range, thus controlling the wavelengths of light exciting the sample. Different filters, called "emission filters", were used to measure the energy of light emitted in certain spectral ranges, by blocking light not having wavelengths in that range. The filters were arranged in cubes consisting of one excitation filter, one emission filter, and a dichroic mirror (see Table I). Autofluorescence separation algorithms according to the present techniques were used to separate the fluorescence due to the beads with that due to tissue. The filter cubes in Table I are intended to measure the fluorescence of a certain dye or to measure autofluorescence, although spectral overlap between dyes' spectra and the autofluorescence spectrum means that each filter cube inevitably measures a combination of these. The filter cubes numbered 1, 2, and 4 in Table I are designed to match the excitation and emission wavelengths of the dyes cy5, cy3, and DAPI (respectively), as closely as possible. On the other hand, the filter cube numbered 3 in Table I has excitation and emission spectra that have a relatively small overlap with those of cy3, cy5, and DAPI. Therefore, filter cube 3 measures more autofluorescence than fluorescence due to dye. Under the assumption that autofluorescence is roughly the same at different wavelengths, filter cube 3 can be used to measure autofluorescence at all wavelengths.

TABLE I

FILTER CUBES USED IN THE EXPERIMENTAL PROTOCOL.

| Filter Cube No. | Vendor | Part number | Excitation filter | Emission filter | Dichroic mirror | Spectra Correspond no. |
|---|---|---|---|---|---|---|
| 1 | Chroma | 41024 | HQ620/60x | HQ665LP | Q660LP | cy5 dye |
| 2 | Zeiss | 43HE | BP550/25 | BP605/70 | 570 | cy3 dye |
| 3 | Semrock | 2432A-000-ZERO | FF01-438/24 | FF01-438/32 | FF458-Di01 | autofluorescence |
| 4 | Zeiss | 49 | 365 | BP445/50 | 395 | DAPI dye |

The outputs from autofluorescence separation algorithms were compared to ground truth images consisting of only fluorescent beads, with no autofluorescence due to tissue. The beads were chosen to fluoresce much more brightly than tissue at the excitation and emission wavelengths of filter cube number 2. Therefore an image taken with that filter cube (see, e.g., FIG. 3A) may be thresholded so that only the beads are visible and tissue autofluorescence is not present. Images taken with filter cube number 2 are ground truth with which algorithm results are compared.

Figure 3C:
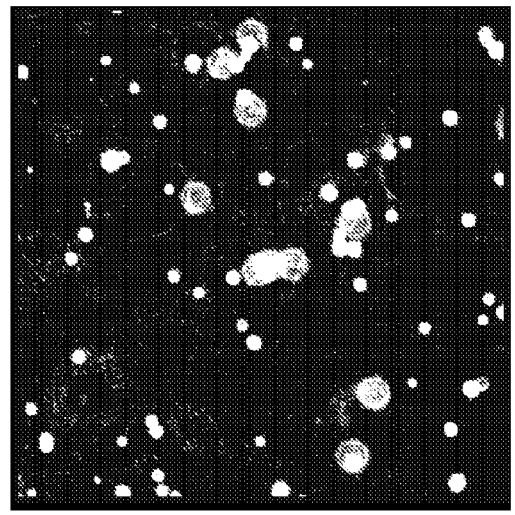
FIG. 3C is an image with the autofluorescence removed according to the present techniques.
Figure 3B:
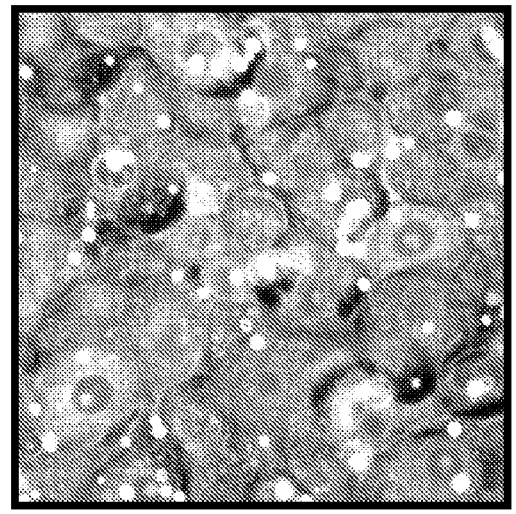
FIG. 3B is an image of the fluorescent beads with autofluorescence.
Figure 3A:
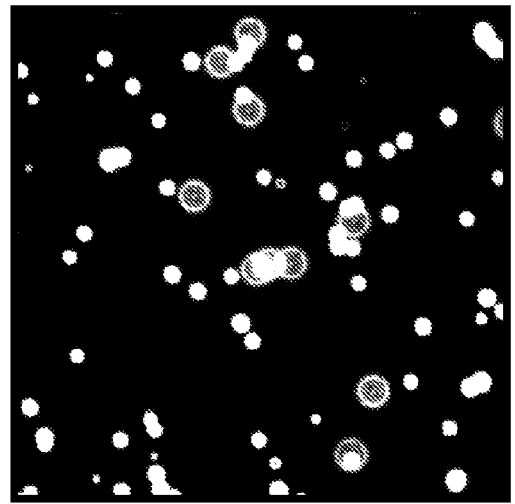
FIG. 3A is a ground truth image of fluorescent beads with no autofluorescence.

The algorithm of the present techniques was applied in the following way. The algorithm was given four images, $I_{OBS}^1$, $I_{OBS}^2$, $I_{OBS}^3$, and $I_{OBS}^4$, defined in equation (3). Of these, $I_{OBS}^1$, $I_{OBS}^2$, and $I_{OBS}^3$, were obtained using filter cubes 1, 2, and 3 (respectively) before the beads were added to the sample. On the other hand, $I_{OBS}^4$, (FIG. 3A) was obtained using filter cube 3, after addition of beads to the sample. In both steps, before and after the beads are added, DAPI images are collected to aid the image registration. Note that the beads are placed on top of a tissue stained with DAPI. The beads were brighter than autofluorescence in the ground truth image (FIG. 3A), the ratio of the beads' brightness to the autofluorescence's brightness in $I_{OBS}^4$ (FIG. 3B) was comparable to the signal to noise ratio in images of stained tissue (FIG. 3A). All four images were represented in the same coordinate system, by registering the DAPI images. The registration was based on minimizing a mutual information metric between the first and the second image. The estimation was done in multiple resolutions from coarse to fine. After 15 iterations of the algorithm of the present techniques, the image $I_{SIG}$ defined in equation (5), was obtained (FIG. 3C). The ground truth image (FIG. 3A) resembles $I_{SIG}$ (FIG. 3C), indicating successful removal of autofluorescence was accomplished. Receiver operator characteristic (ROC) analysis was used to quantify that similarity. More specifically, a threshold was chosen such that pixels above that threshold in the ground truth image (FIG. 3A) belong to a bead, and pixels below that threshold do not. In addition, $I_{SIG}$ (FIG. 3C) was thresholded at a variable threshold t, that took 100 values between the minimum and maximum pixel values in $I_{SIG}$. For each value of t, those pixels whose value exceeded t were predicted by the algorithm to be beads. By comparison with the thresholded ground truth image (FIG. 3A), a false positive rate and a true positive rate were calculated, for each value of t.

The algorithm of the present techniques was compared to other techniques such as image subtraction, non-normalized nonnegative matrix factorization, and principal component analysis by two-sample t-tests. The results were plotted as a receiver operator characteristic (ROC) curve, as shown in FIG. 4. This procedure was repeated 35 times, for 35 different tissue samples. The mean of the 35 ROC curves was calculated. The areas under 35 ROC curves (AUC) were calculated for normalized non-negative matrix factorization (reference 40), image subtraction (reference 42), non-normalized non-negative matrix factorization (reference 44), and principal component analysis (reference 46). Three t-tests were performed. Each t-test compared the areas under 35 ROC curves for a previous state of the art method, with the areas under 35 ROC curves for the algorithm of the present paper. In each case, the results were significant, with a p-value less than 0.01, showing that the present techniques lead to higher AUCs than previous methods (Table II). The usefulness of the dark current matrix D (Subsection II-D) was demonstrated by comparing the normalized, non-negative matrix factorization to the non-normalized, non-negative matrix factorization with no D term in the model. Exactly the same inputs and validation procedure were used, but the matrix D was omitted from the algorithm.

TABLE II

| Method | Significance level (p-value) |
|---|---|
| Image substraction | 7.8E−06 |
| Non-normalized Non-negative matrix factorization | 3.6E−11 |
| Principal component analysis | 2.9E−08 |

Figure 5B:
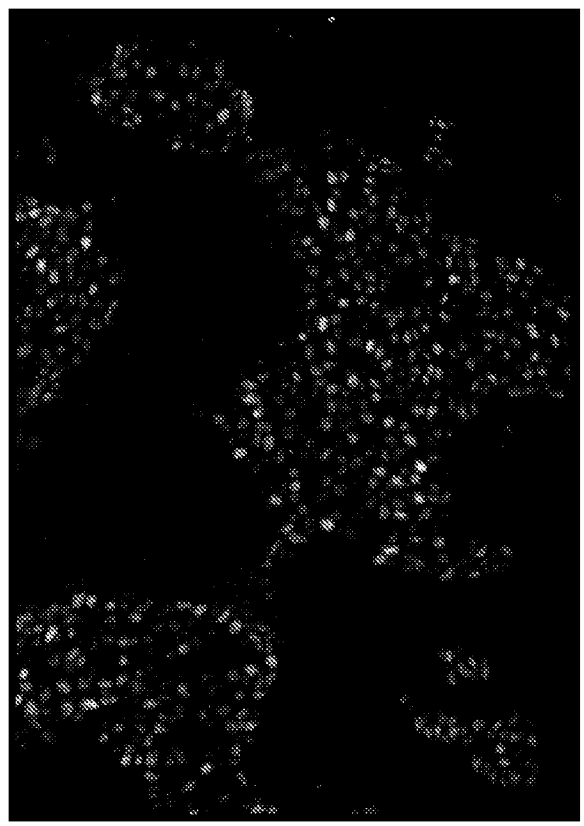
FIG. 5B is the image of FIG. 5A with the autofluorescence removed according to the present techniques.
Figure 5A:
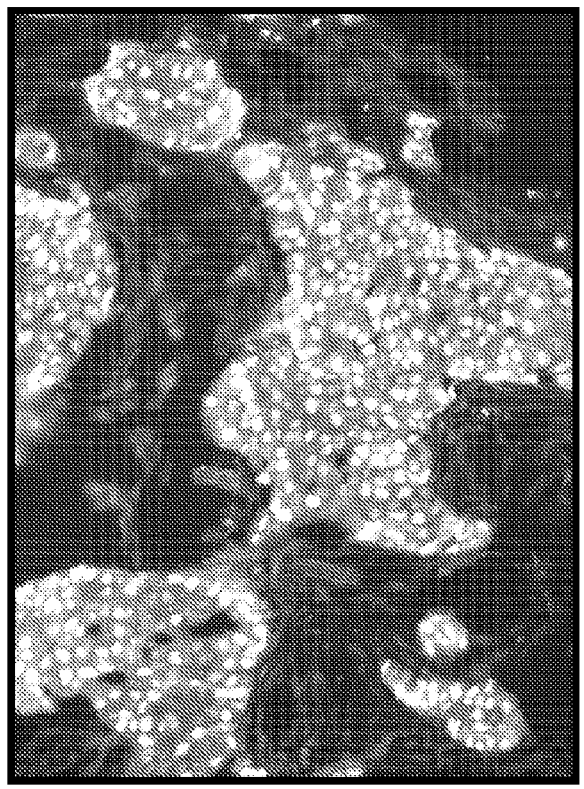
FIG. 5A is an image of a human breast tissue sample sainted with cy5 bound to estrogen receptor.

FIGS. 5A and 5B are examples of an input and an output, respectively, for the present techniques. FIG. 5A is an image of a human breast biopsy stained with Cy5 bound to estrogen receptor, as well as autofluorescence due to tissue. After 15 iterations of the presently disclosed algorithm, the output $I_{SIG}$, defined in equation (5), was obtained (FIG. 5B). This image is an estimate for the fluorescence due to Cy5, without the autofluorescence due to tissue.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for reducing autofluorescence in an image of a biological material, comprising the steps of:
    accessing image data from two or more images of the biological material, wherein at least one of the images is fluorescently stained for a marker of interest and wherein at least one of the images is a reference image;
    analyzing the image data of the two or more images using a non-negative matrix factorization algorithm to generate an estimate of the autofluorescence in at least one of the two or more images; and
    generating an output of a corrected image with reduced autofluorescence.

2. The method of claim 1, comprising iteratively improving the estimate of the autofluorescence.

3. The method of claim 2, wherein iteratively improving the estimate of the autofluorescence comprises smoothing with a Gaussian kernel.

4. The method of claim 1, wherein the non-negative matrix factorization algorithm comprises an estimate for the contribution of dark current.

5. The method of claim 1, wherein the non-negative matrix factorization algorithm uses as an input the camera exposure time for each of the two or more images.

6. The method of claim 1, wherein analyzing the image data comprises employing an alternating constrained least squares approach.

7. The method of claim 1, comprising acquiring the two or more images by a two-step image acquisition or an extra channel image acquisition.

8. A non-transitory computer-readable medium comprising instructions for:
   accessing image data from two or more images of the biological material, wherein at least one of the images is fluorescently stained for a marker of interest and wherein at least one of the images is a reference image;
   analyzing the image data of the two or more images using a non-negative matrix factorization algorithm to generate an estimate of the autofluorescence in at least one of the two or more images; and
   generating an output of a corrected image with reduced autofluorescence.

9. The non-transitory computer-readable medium of claim 8, comprising instructions for iteratively improving the estimate of the autofluorescence.

10. The non-transitory computer-readable medium of claim 9, wherein the instructions for iteratively improving the estimate of the autofluorescence comprise smoothing with a Gaussian kernel.

11. The non-transitory computer-readable medium of claim 8, wherein the non-negative matrix factorization algorithm comprises an estimate for the contribution of dark current.

12. The non-transitory computer-readable medium of claim 8, wherein the non-negative matrix factorization algorithm uses as an input the camera exposure time for each of the two or more images.

13. The non-transitory computer-readable medium of claim 8, wherein the instructions for analyzing the image data comprise employing an alternating constrained least squares approach.

14. The non-transitory computer-readable medium of claim 8, comprising instructions for acquiring the two or more images by a two-step image acquisition, or an extra channel image acquisition.

15. An image analysis system comprising:
   a processor adapted to receive image data from two or more images of the biological material, wherein at least one of the images is fluorescently stained for a marker of interest and wherein at least one of the images is a reference image the processor adapted to run instructions for:
      analyzing the image data of the two or more images using a non-negative matrix factorization algorithm to generate an estimate of the autofluorescence in at least one of the two or more images; and
      generating an output of a corrected image with reduced autofluorescence.

16. The system of claim 15, comprising instructions for iteratively improving the estimate of the autofluorescence.

17. The system of claim 16, wherein the instructions for iteratively improving the estimate of the autofluorescence comprise smoothing with a Gaussian kernel.

18. The system of claim 15, wherein the non-negative matrix factorization algorithm comprises an estimate for the contribution of dark current.

19. The system of claim 15, wherein the non-negative matrix factorization algorithm uses as an input the camera exposure time for each of the two or more images.

20. The system of claim 15, wherein the instructions for analyzing the image data comprise employing an alternating constrained least squares approach.

21. The system of claim 15, comprising instructions for acquiring the two or more images by a two-step image acquisition or an extra channel image acquisition.

* * * * *